United States Patent [19]

Rokach et al.

[11] 4,252,818

[45] Feb. 24, 1981

[54] NOVEL BENZOPYRAN DERIVATIVES

[75] Inventors: Joshua Rokach, Chomedey-Laval; Pierre A. Hamel, Vimont-Laval, both of Canada; Ralph F. Hirschmann, Blue Bell, Pa.

[73] Assignee: Merck & Co., Inc., Rahway, N.J.

[21] Appl. No.: 63,020

[22] Filed: Aug. 2, 1979

[51] Int. Cl.$^3$ .................... C07D 311/22; A61K 31/35
[52] U.S. Cl. ................. 424/283; 260/345.2; 260/348.15; 568/310; 568/315
[58] Field of Search ...................... 260/345.2; 424/283

[56] References Cited
U.S. PATENT DOCUMENTS 3,882,148   5/1975   Augstein et al. ................. 260/345.2

OTHER PUBLICATIONS

Augstein et al., Nature New Biology, 245,215, (1973).
Augstein et al., Chemical Abstract, 83, P147,393c, (1975).

*Primary Examiner*—Nicky Chan
*Attorney, Agent, or Firm*—Frank M. Mahon; Julian S. Levitt; Thomas E. Arther

[57] ABSTRACT

7-[3-(4-Acetyl-3-hydroxy-6-iodo-2-propylphenoxy)-2-hydroxypropoxy]-4-oxo-8-propyl-4H-1-benzopyran-2-carboxylic acid and its pharmaceutically acceptable salts are employed as antagonists of SRS-A (the slow reacting substance of anaphylaxis) in the treatment of asthma and allergic diseases.

5 Claims, No Drawings

NOVEL BENZOPYRAN DERIVATIVES

SUMMARY OF THE INVENTION

The instant invention relates to novel compounds showing enhanced antagonist activity against SRS-A. More particularly, the instant invention relates to new benzopyran (chromone) derivatives; to methods of preparing such compounds; and to methods of employing them in the treatment and control of asthma and allergic diseases.

In its composition of matter aspect, the instant invention may be described as residing in the concept of novel benzopyran derivatives characterized by having the following structural formula:

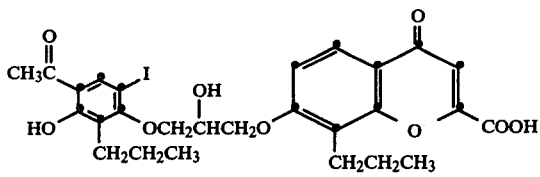

and the pharmaceutically acceptable salts thereof.

Chromone compounds having SRS-A antagonist activity have been described in the chemical and patent literature. U.S. Pat. No. 3,882,148, issued May 6, 1975, broadly discloses and discloses and claims a group of chromone derivatives having this utility. Among these, the sodium salt of 7-[3-(4-acetyl-3-hydroxy-2-propylphenoxy)-2-hydroxypropoxy]-4-oxo-8-propyl-4H-1-benzopyran-2-carboxylic acid has been described in the literature as a potent, selective and dose dependent antagonist of SRS-A. The chromone derivative of formula I, however, was not known and described in the literature prior to applicants' discovery thereof.

The instant invention is based upon applicants' discovery that 7-[3-(4-acetyl-3-hydroxy-6-iodo-2-propylphenoxy)-2-hydroxypropoxy]-4-oxo-8-propyl-4H-1-benzopyran-2-carboxylic acid, the compound of formula I and its pharmaceutically acceptable salts not only display SRS-A antagonist activity but, surprisingly, are more potent antiasthma agents; have superior antihistaminic properties; are longer acting and have fewer side effects than chromone derivatives heretofore described.

It is contemplated, therefore, that dosage units containing the chromone of formula I or its pharmaceutically acceptable salts as the essential active ingredient will be employed in the treatment and control of a variety of conditions in humans and warm-blooded animals where excessive contractile activity of SRS-A occur. Such formulations, thus, find application in allergic diseases such as, for example, asthma, hay fever and inflammation.

The chromone derivative of formula I is readily prepared according to the following reaction scheme:

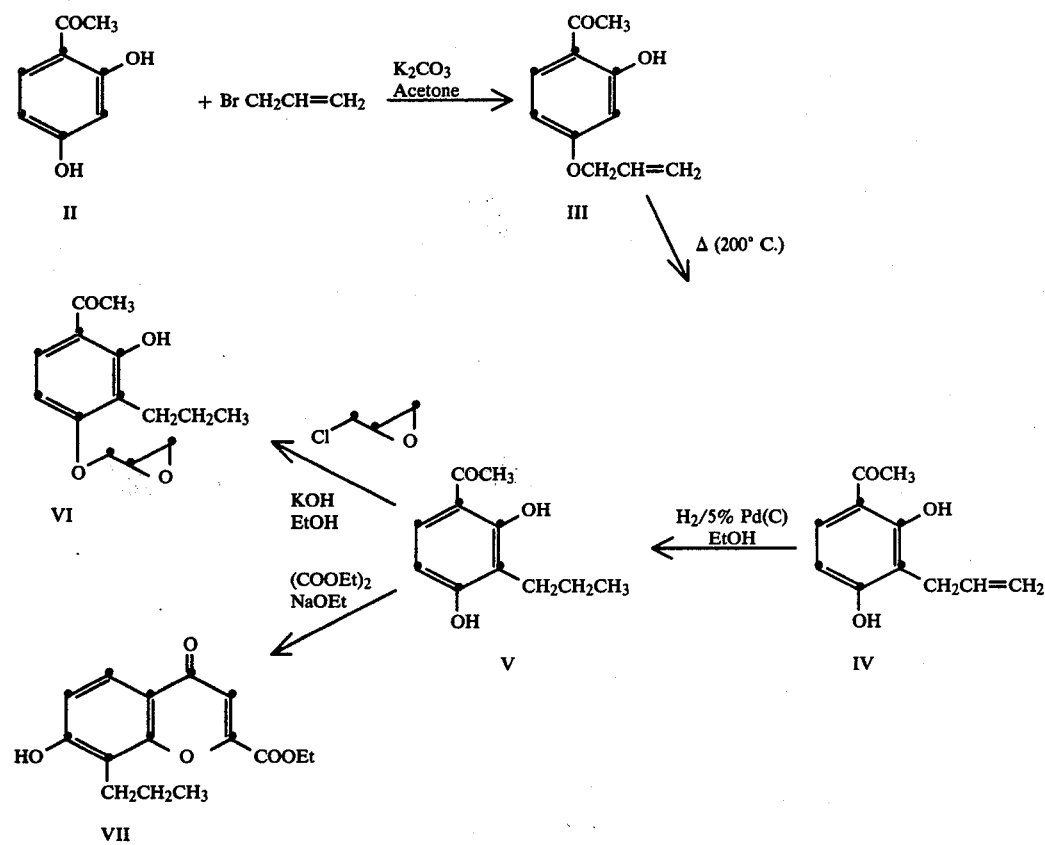

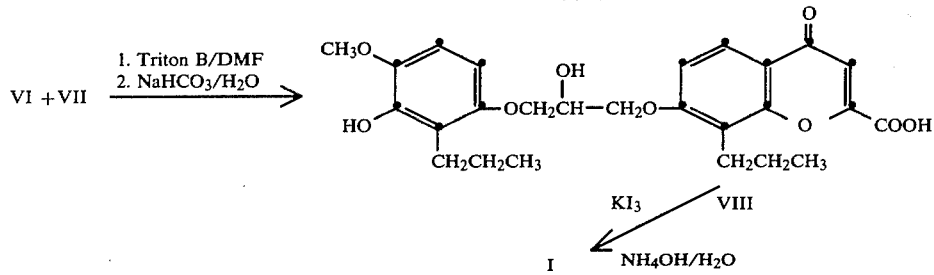

by reacting 2,4-dihydroxyacetophenone (II) with allylbromide in the presence of potassium carbonate and acetone to obtain 4-allyloxy-2-hydroxyacetophenone III which, upon heating at 180°–220° C., undergoes rearrangement to form 3-allyl-2,4-dihydroxyacetophenone (IV). The dihydroxy intermediate then is catalytically reduced in the presence of palladium/carbon catalyst to form 2,4-dihydroxy-3-propylacetophenone (V). Intermediate (V) then is treated with epichlorohydrin in refluxing ethanolic potassium hydroxide to form 4-(2,4-epoxypropoxy)-2-hydroxy-3-propylacetophenone (VI) and with diethyl oxalate in the presence of sodium ethoxide to form ethyl 7-hydroxy-8-propyl-4-oxo-4H-1-benzopyran-2-carboxylate (VII). Intermediates (VI) and (VII) are reacted under a nitrogen atmosphere at 140°–150° C. in the presence of Triton B (Rohm & Hass, Philadelphia, Pa.) and the resulting ester treated with sodium bicarbonate to form 7-[3-(4-acetyl-3-hydroxy-2-propylphenoxy)-2-hydroxypropoxy]-4-oxo-8-propyl-4H-1-benzopyran-2-carboxylic acid (VIII). This intermediate, preferably the sodium salt, then is iodinated in the presence of potassium triiodide to form the desired 7-[3-(4-acetyl-3-hydroxy-6-iodo-2-propylphenoxy)-2-hydroxypropoxy]-4-oxo-8-propyl-4H-1-benzopyran-2-carboxylic acid (I).

Alternatively, the iodo group can be introduced prior to the last step of the synthesis and the chromone derivative of formula I prepared according to the following reaction scheme:

refluxing ethanolic potassium hydroxide to form 4-(2,3-epoxypropoxy)-2-hydroxy-3-propyl-5-iodoacetophenone (X). Reaction of intermediate (X) with ethyl 7-hydroxy-8-propyl-4-oxo-4H-1-benzopyran-2-carboxylate (intermediate VII, above) in the presence of Triton B yields ethyl 7-[3-(4-acetyl-3-hydroxy-6-iodo-2-propylphenoxy)-2-hydroxypropoxy]-4-oxo-8-propyl-4H-1-benzopyran-2-carboxylate (XI) which is hydrolyzed to obtain the desired chromone derivative of formula I.

As noted above, pharmaceutically acceptable salts of the novel chromones also are included within the scope of this invention. The term, pharmaceutically acceptable salts, is intended to include salts derived from pharmaceutically acceptable non-toxic bases such as, for example, ammonium salts, alkali metal salts such as sodium and potassium salts, alkaline earth metal salts such as magnesium and calcium salts, salts of organic bases such as amine salts derived from mono-, di and tri-loweralkyl or loweralkanoyl amines such as trimethylamine, dimethylamine and triethanolamine and salts derived from heterocyclic amines such as piperidine, pyridine, piperazine and morpholine.

The best mode contemplated by applicants for carrying out their invention is illustrated in the following working Examples. No limitation, however, is intended except as set forth in the appended claims.

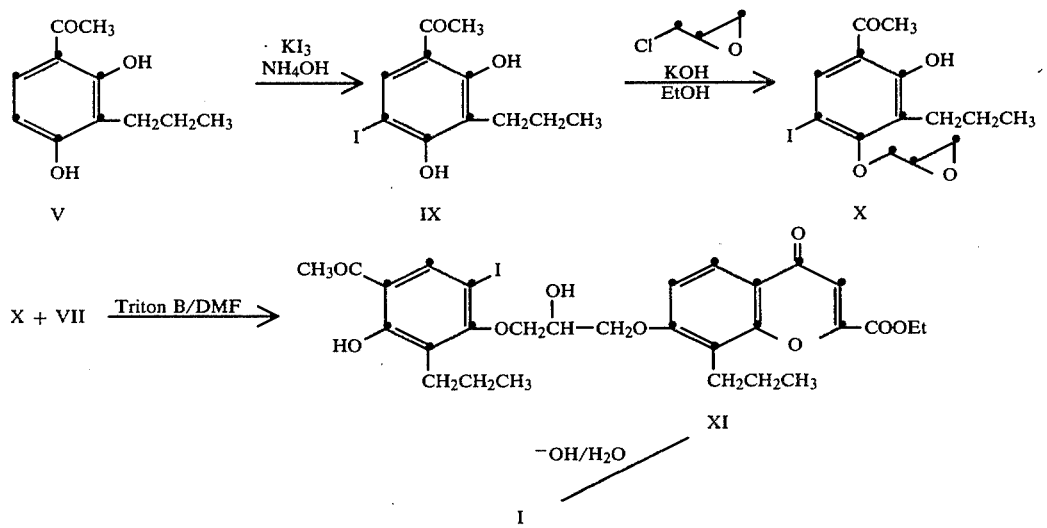

by iodinating 2,4-dihydroxy-3-propylacetophenone (intermediate V, above) in the presence of potassium triiodide to form 2,4-dihydroxy-5-iodo-3-propylacetophenone (IX) which then is treated with epichlorohydrin in

EXAMPLE 1

7-[3-(4-Acetyl-3-hydroxy-6-iodo-2-propylphenoxy)-2-hydroxypropoxy]-4-oxo-8-propyl-4H-1-benzopyran-2-carboxylic Acid

Step A: 4-Allyloxy-2-hydroxyacetophenone

Mix 100 gm of 2,4-dihydroxyacetophenone, 88 gm of allyl bromide and 120 gm of potassium carbonate in 250 ml of acetone. Reflux while stirring overnight. Filter and strip the residue to dryness. Dissolve the residue in 700 ml of ether and add 250 ml of 4 N aqueous sodium hydroxide. Separate the solids by filtration and wash with ether. Suspend the solids in a mixture of water and ether (1:1) and acidify with 10% aqueous hydrochloric acid. Separate the ether layer and extract the aqueous layer with ether. Combine the ether extracts, wash with water, dry and strip to an oil (yield 100.2 gm) which is employed in the next step without further purification.

Step B: 3-Allyl-2,4-dihydroxyacetophenone

Heat 50 gm of the 4-allyloxy-2-hydroxyacetophenone of Step A at 210°-220° under a nitrogen atmosphere with stirring for 8 hours. Cool and boil the residue in 250 ml of carbon tetrachloride. Cool and allow the residue to stand overnight. Separate the solids by filtration to obtain the title product. (mp 132°-134° C.)

Step C: 2,4-Dihydroxy-3-propylacetophenone

Dissolve 9.6 gm of 3-allyl-2,4-dihydroxyacetophenone in 100 ml of ethanol; flush with nitrogen and add 0.5 gm of 5% palladium/charcoal catalyst. Hydrogenate in a Parr apparatus at room temperature until 45 p.s.i. of hydrogen is taken up. Filter and strip the filtrate to dryness to obtain the title product. (mp 125°-127° C.)

Step D: 4-(2,3-epoxypropoxy)-2-hydroxy-3-propylacetophenone

Add dropwise a solution of 10.9 gm of potassium hydroxide in 50 ml of absolute ethanol containing 1 ml of water to a refluxing solution of 35 gm of 2,4-dihydroxy-3-propylacetophenone and 42.5 ml of epichlorohydrin in 30 ml of absolute ethanol. Reflux the mixture for 2 hours; cool; extract twice with ether. Combine the ether extracts; wash with water and dry over sodium sulfate. Evaporate to a residue and distill the residue under reduced pressure. Collect the title product at 140°-145° C./2.0-2.5 mm and cool. (yield 26.5 gm)

Step E: Ethyl 7-Hydroxy-8-propyl-4-oxo-4H-1-benzopyran-2-carboxylate

To a solution of sodium ethoxide (from 19 gm. of sodium and 260 ml of absolute ethanol) under nitrogen atmosphere, add dropwise a solution of 40 gm of 2,4-dihydroxy-3-propylacetophenone and 68 gm of diethyloxalate in 55 ml of absolute ethanol and 55 ml of absolute ether. Heat under reflux for 3.5 hours. Cool to room temperature and pour the mixture into 500 ml of 5% aqueous hydrochloric acid. Extract the mixture twice with ether. Wash the combined organic fractions with water, dry over sodium sulfate and strip to a residue. Reflux the residue for 30 minutes in 150 ml absolute ethanol containing 2.5 ml of concentrated hydrochloric acid. Evaporate most of the ethanol and partition the residue between water and ethyl acetate. Wash the organic fraction with water, aqueous sodium bicarbonate solution and again with water. Dry over sodium sulfate and strip to a residue. Crystallize the residue from ethyl acetate-hexane to obtain a first crop (mp 155°-162° C.). Strip the mother liquors to dryness and chromatograph the residue over silica gel, eluting with a mixture of ethylacetate-hexane (1:1). Crystallize the resulting product from ethyl acetate to obtain a second crop. (mp 165°-167° C. lit. 166°-167° C.).

Step F: 7-[3-(4-Acetyl-3-hydroxy-2-propylphenoxy)-2-hydroxypropoxy]-4-oxo-8-propyl-4H-1-benzopyran-2-carboxylic Acid Dissolve 26 gm of 4-(2,3-epoxypropoxy)-2-hydroxy-3-propylacetophenone and 26 gm of ethyl 7-hydroxy-8-propyl-4-oxo-4H-1-benzopyran-2-carboxylate in 150 ml of N,N-dimethylformamide and add 5 drops of Triton B (benzyltrimethylammonium hydroxide 40% in methanol). Heat at 140°-150° C. under nitrogen for 4 hours. Cool the mixture and pour into 1200 ml of water. Extract three times with 400 ml of ethyl acetate. Wash the combined organic fractions with water, then twice with 250 ml of 2% aqueous sodium hydroxide and again with water. Dry over sodium sulfate and strip to a residue. Chromatograph the residue over silica gel (1200 gm), eluting with a mixture of toluene-ethyl acetate (10:1). Dissolve the ester product (30 gm) in 1 liter of ethanol and add 30 gm of sodium bicarbonate and 100 ml of water. Reflux for 2 hours. Evaporate most of the solvent and partition the residue between ethyl acetate and 5% aqueous sodium hydroxide. Acidify the aqueous fraction and extract into ethyl acetate. Strip the extract to a residue and triturate the residue in 300 ml of ether. Recover the solids by filtration. (mp 199°-201° C.).

PREPARATION OF SODIUM SALT

Dissolve 3 gm of free acid product in 50 ml of absolute ethanol and add 5.9 ml of standardized aqueous 1 M sodium hydroxide. Stir for 10 minutes at room temperature. Strip the mixture to dryness and flush the residue four times with ethanol and twice with toluene.

Step G: 7[3-(4-Acetyl-3-hydroxy-6-iodo-2-propylphenoxy)-2-hydroxypropoxy]-4-oxo-8-propyl-4H-1-benzopyran-2-carboxylic Acid Dissolve 10.9 gm of 7-[3-(4-acetyl-3-hydroxy-2-propylphenoxy)-2-hydroxypropoxy]-4-oxo-8-propyl-4H-1-benzopyran-2-carboxylic acid sodium salt in 250 ml of 28% ammonium hydroxide solution. Cool the mixture in an ice-water bath. Add 285 ml of a 0.2 m aqueous potassium triiodide solution dropwise. Stir in the cold for 15 minutes. Add sodium bisulfite until iodine color is discharged. Acidify the mixture slowly with 20% aqueous hydrochloric acid. Separate the solids by filtration, wash with water and dry. Dissolve the solids in methanol and esterify with diazomethane in ether. Chromatograph on silica gel, eluting with 15% ethyl acetate in toluene (mp 137°-141° C.). Crystallize from toluene (mp 150°-153° C.). Reflux 2.1 gm of ester product in a mixture of 2.1 gm of sodium bicarbonate, 200 ml of denatured alcohol and 20 ml of water for 1 hour. Strip the mixture to dryness and triturate the residue in ethyl acetate. Separate the solids, dissolve in water and acidify with 10% aqueous hydrochloric acid. Separate the solids by filtration. (mp 179°-182° C.)

EXAMPLE 2

7[3-(4-Acetyl-3-hydroxy-6-iodo-2-propylphenoxy)-2-hydroxypropoxy]-4-oxo-8-propyl-4H-1-benzopyran-2-carboxylic Acid Step A: 2,4-Dihydroxy-5-iodo-3-propylacetophenone Dissolve 2.33 gm of 2,4-dihydroxy-3-propylacetophenone in 25 ml of alcohol and 25 ml of ammonium hydroxide and cool the mixture in an ice-bath. Keeping the temperature at 5°-10° C., add 130 ml of potassium triiodide solution (prepared by stirring 7.47 gm. of potassium iodide and 7.62 gm of iodine in 300 ml of water for 20 hours). With continued cooling, acidify the mixture with 10% aqueous hydrochloric acid. Extract into ether. Wash the organic phase with water, then with aqueous sodium bisulfite and again with water. Dry over sodium sulfate and strip to a residue. Chromatograph over silica gel, eluting with 5% ethyl acetate in toluene. (yield 2.87 gm., 74.7%)

Step B: 4-(2,3-Epoxypropoxy)-2-hydroxy-5-iodo-3-propylacetophenone

Add a solution containing 317 mg of potassium hydroxide in 3-4 ml of absolute ethanol containing 0.25 ml of water to a refluxing solution of 1.69 gm of 2,4-dihydroxy-5-iodo-3-propylacetophenone and 1.24 ml of epichlorohydrin in 10 ml of absolute ethanol. Reflux for 3 hours. Cool the reaction mixture, dilute with water and extract into ether. Chromatograph the ether extract over silica gel, eluting with 5% ethyl acetate in toluene. (yield 1.1 gm, 55% thick yellow oil)

Step C: 7-[3-(4-Acetyl-3-hydroxy-6-iodo-2-propylphenoxy)-2-hydroxypropoxy]-4-oxo-8-propyl-4H-1-benzopyran-2-carboxylic Acid Dissolve 310 mg of 4-(2,3-epoxypropoxy)-2-hydroxy-5-iodo-3-propylacetophenone and 227 mg of ethyl-7-hydroxy-8-propyl-4-oxo-4H-1-benzopyran-2-carboxylate in 1.5 ml of N,N-dimethylformamide and add 1 drop of Triton B. Reflux for 90 minutes. Dilute with water and ethyl acetate. Acidify with a few drops of concentrated hydrochloric acid. Shake and separate the organic layer. Again extract the aqueous layer with ethyl acetate. Combine the ethyl acetate extracts, wash with water then twice with 2% aqueous sodium hydroxide and again with water. Dry the extract and strip to a residue. Chromatograph over silica gel, eluting with (1:1) ethylacetate/toluene. Dissolve the ester so produced in 10 ml of ethanol and add 100 mg of sodium bicarbonate in 1 ml of water. Heat at 80°-85° C. for 2 hours. Evaporate most of the ethanol and partition the residue between water and ether. Separate the solids formed at the interface by filtration. Dissolve in warm water, acidify and separate the solids by filtration. (mp 173°-176° C.)

As pointed out above, the chromone of formula I and its pharmaceutically acceptable salts are useful in the treatment and control of a variety of conditions in humans and warm-blooded animals where excessive contractile activity of SRS-A occur. These conditions include, for example, allergic diseases such as asthma, hay-fever as well as inflammatory states such as arthritis and skin afflictions.

The magnitude of a prophylactic or therapeutic dose of compound of formula I will, of course, vary with the nature of the severity of the condition to be treated and with the particular compound of formula I and its route of administration. In general, the daily dose range lies within the range of 0.2 mg. to 100 mg. per kg. body weight of a mammal.

The pharmaceutical compositions of the present invention comprise a compound of formula I as an active ingredient, and may also contain a pharmaceutically acceptable carrier and optionally other therapeutic ingredients. The compositions include compositions suitable for oral, rectal, opthalmic, pulmonary, nasal, dermal, topical or parenteral (including subcutaneous, intramuscular and intravenous) administration, although the most suitable route in any given case will depend on the nature and severity of the condition being treated and on the nature of the active ingredient. They may be conveniently presented in unit dosage form and prepared by any of the methods well-known in the art of pharmacy.

For use where a composition for intravenous administration is employed, a suitable dosage range is from 0.2 to 20 mg. (preferably 1 to 10 mg.) of a compound of formula I per kg. of body weight per day and in the case where an oral composition is employed a suitable dosage range is about, e.g., 1 to 50 mg. of a compound of formula I per kg. of body weight per day, preferably from 5 to 40 mg./kg.

Pharmaceutical compositions of the present invention suitable for oral administration and by inhalation in the case of asthma therapy may be presented as discrete units such as capsules, cachets or tablets each containing a predetermined amount of the active ingredient; as a powder or granules; or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent. Desirably, each tablet contains from 25 mg. to 500 mg. of the active ingredient and each cachet or capsule contains from 25 mg. to 500 mg. of the active ingredient.

Although the instant invention has been described above with particular reference to the chromone of formula I and its pharmaceutically acceptable salts, and to the use of these compounds in the treatment and control of conditions wherein excessive contractile activity of SRS-A occurs, many modifications will suggest themselves to those skilled in the art from a study of the foregoing specification. It will be obvious, for example, that halogens other than iodine (e.g., bromine, chlorine and fluorine) could be introduced at the 6-position and resulting 6-chloro, 6-bromo, and 6-fluoro chromone derivatives could be employed for the same purposes and in the same manner as described above for the 6-iodo compound. Applicants consider all such obvious modifications to be the full equivalent of the chromone of formula I and to fall within the scope of the instant invention.

The subject matter which applicants regard as their invention, and which is sought to be patented herein, is particularly pointed out and distinctly claimed as follows:

1. A compound of the formula:

[Structure I: CH₃C(O)-, HO-, I, CH₂CH₂CH₃ substituted phenyl-OCH₂CH(OH)CH₂O- linked to 8-propyl-4-oxo-4H-1-benzopyran-2-carboxylic acid]

and the pharmaceutically acceptable salts thereof.

2. The compound of claim 1 which is 7-[3-(4-acetyl-3-hydroxy-6-iodo-2-propylphenoxy)-2-hydroxypropoxy]-4-oxo-8-propyl-4H-1-benzopyran-2-carboxylic acid.

3. The compound of claim 1 which is 7-[3-(4-acetyl-3-hydroxy-6-iodo-2-propylphenoxy)-2-hydroxypropoxy]-4-oxo-8-propyl-4H-1-benzopyran-2-carboxylic acid sodium salt.

4. A composition for the treatment and control of undesirable contractile activity of SRS-A consisting essentially of a pharmaceutically acceptable carrier and a therapeutically effective amount of a compound of the formula:

[Structure I]

and the pharmaceutically acceptable salts thereof.

5. A method for the treatment and control of undesirable contractile activity of SRS-A which comprises administering to a host in need of such treatment a pharmaceutical formulation consisting essestially of a pharmaceutically acceptable carrier and a therapeutically effective amount of a compound of the formula:

[Structure I]

and the pharmaceutically acceptable salts thereof.

* * * * *